United States Patent
Milgram et al.

(10) Patent No.: US 11,074,330 B2
(45) Date of Patent: Jul. 27, 2021

(54) BIOMETRIC RECOGNITION METHOD

(71) Applicant: IDEMIA IDENTITY & SECURITY FRANCE, Courbevoie (FR)

(72) Inventors: Jonathan Milgram, Courbevoie (FR); Stéphane Gentric, Courbevoie (FR)

(73) Assignee: IDEMIA IDENTITY & SECURITY FRANCE, Courbevoie (FR)

( * ) Notice: Subject to any disclaimer, the term of this patent is extended or adjusted under 35 U.S.C. 154(b) by 33 days.

(21) Appl. No.: 16/510,399

(22) Filed: Jul. 12, 2019

(65) Prior Publication Data
US 2020/0019691 A1 Jan. 16, 2020

(30) Foreign Application Priority Data
Jul. 13, 2018 (FR) ...................... 1856529

(51) Int. Cl.
*G06K 9/00* (2006.01)
*G06F 21/32* (2013.01)
*G07C 9/37* (2020.01)
*A61B 5/1171* (2016.01)

(52) U.S. Cl.
CPC ......... *G06F 21/32* (2013.01); *G06K 9/00288* (2013.01); *A61B 5/1176* (2013.01); *G06K 9/00885* (2013.01); *G07C 9/37* (2020.01)

(58) Field of Classification Search
CPC ............. G06F 21/32; G06K 9/00288; G06K 9/00885; G06K 9/4628; G06K 9/00221; G07C 9/37; A61B 5/1176
See application file for complete search history.

(56) References Cited

U.S. PATENT DOCUMENTS

| | | | |
|---|---|---|---|
| 2003/0095689 A1 | 5/2003 | Vollkommer et al. | |
| 2017/0351909 A1* | 12/2017 | Kaehler | G06K 9/00456 |
| 2018/0101742 A1* | 4/2018 | Burge | G06K 9/00926 |
| 2019/0205620 A1* | 7/2019 | Yi | G06K 9/6262 |
| 2019/0311261 A1* | 10/2019 | Baldwin | G06N 3/049 |
| 2020/0257889 A1* | 8/2020 | Merkel | G06K 9/00268 |

OTHER PUBLICATIONS

Buchmann et al., "BioPACE: Biometric-Protected Authentication Connection Establishment", http://www.dasec.h-da.de/wp-content/uploads/2014/03/bace.pdf, Dec. 13, 2013, 24 pages.

Hasnat et al., "DeepVisage: Making face recognition simple yet with powerful generalization skills", IEEE International Conference on Computer Vision Workshops, 2017, 10 pages.

* cited by examiner

*Primary Examiner* — Ping Y Hsieh
(74) *Attorney, Agent, or Firm* — Muncy, Geissler, Olds & Lowe, P.C.

(57) ABSTRACT

A biometric recognition method comprising the step of calculating a similarity score between a candidate biometric vector and a reference biometric vector, at least one of the two biometric vectors being quantified.

14 Claims, 1 Drawing Sheet

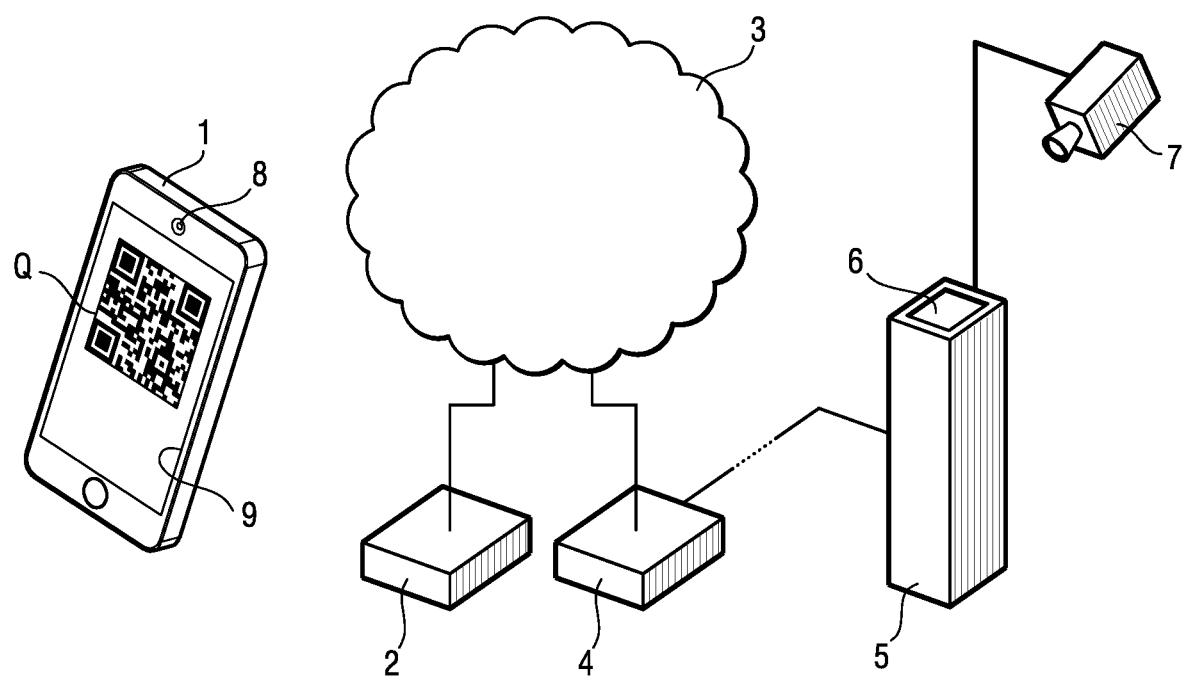

BIOMETRIC RECOGNITION METHOD

The present invention relates to the field of biometric recognition, e.g. for the purposes of identifying an individual or for verifying an individual's right to access premises or information.

TECHNOLOGICAL BACKGROUND

Conventionally, a biometric recognition method comprises the following steps:
  capturing an image of a portion of the body of a candidate for recognition;
  extracting from that image biometric characteristics in the form of a biometric vector of the candidate;
  calculating a similarity score between the biometric vector of the candidate and a reference biometric vector stored in a database hosted by a computer or in a data medium held by the candidate, such as an integrated circuit incorporated in a data card or in an identity document such as a passport; and
  validating or refusing recognition as a function of the similarity score.

The reference biometric vector is obtained during an enrollment operation that comprises the following steps:
  capturing an image of a portion of the body of a candidate for enrollment; and
  extracting from this image biometric characteristics in the form of a reference biometric vector that is stored in the database hosted by a computer or in the data medium held by the candidate.

At present, the reference biometric vector occupies a relatively large amount of space in the memory of the data medium, even though the size of that memory is relatively limited.

OBJECT OF THE INVENTION

An object of the invention is to provide means for remedying the above problem, or more generally, for limiting at least in part the resources needed for biometric recognition.

BRIEF SUMMARY OF THE INVENTION

To this end, the invention provides a biometric recognition method comprising:
  during an enrollment stage, the steps of:
  capturing an image of a portion of an individual's body; and
  extracting from that image biometric characteristics in the form of a reference biometric vector; and
  during a recognition stage, the steps of:
  capturing an image of a portion of the body of a candidate for recognition;
  extracting from that image biometric characteristics in the form of a candidate biometric vector;
  calculating a similarity score between the candidate biometric vector and the reference biometric vector, one of the two biometric vectors being quantified; and
  validating or refusing recognition as a function of the similarity score.

Other characteristics and advantages of the invention appear on reading the following description of a particular, non-limiting implementation of the invention.

BRIEF DESCRIPTION OF THE DRAWINGS

Reference is made to the sole accompanying FIGURE, which is a perspective view of a device for performing the invention.

DETAILED DESCRIPTION OF THE INVENTION

The invention is described here in application to aircraft access control at an airport. Access to the aircraft requires a boarding pass mentioning at least:
  the identification elements of the aircraft and the flight;
  the passenger's full name and surname.

The boarding pass is traditionally issued by an automatic terminal from a reservation number or other identification information, or at the ticket office of the airline that chartered or owns the aircraft.

In the implementation mode that will be described, a biometric reference vector is associated with a personal document and more particularly here, with the boarding pass.

This is perfectly feasible with a "paper" boarding pass but, in the implementation described here, the boarding pass is dematerialized.

To this end, and with reference to the FIGURE passengers with a mobile phone 1 of the "computer" or "smartphone" types are offered the downloading of an application to edit the boarding pass. This application is downloaded from a computer server 2 belonging to the airline owning or chartering the aircraft. The computer server 2 typically consists of a processor and a memory containing programs, and is connected to a data transport network 3, such as the Internet, which the mobile phone 1 can connect to.

The mobile phone 1 is of the conventional type and includes a processor, a memory containing programs (some of which are commonly called applications), and at least one image sensor 8.

The computer server 2 runs a program comprising instructions for selling airline tickets. To buy an airline ticket, the future passenger must identify himself/herself on the computer server 2, select the desired flight, then pay. The program then suggests that he/she should download the application to his/her mobile phone 1 so that he/she can create his/her boarding pass.

When the downloaded application is executed, it commands a connection from the mobile phone 1 to the computer server 2 to be made to:
  perform a passenger authentication process (entering a username and a password) and then,
  if the authentication is successful, perform a process to create the boarding pass.

The process of creating the boarding pass includes the steps of:
  capturing an image of a part of the body of an enlistment candidate;
  extracting biometric characteristics from this image in the form of an initial biometric reference vector;
  quantifying the initial biometric reference vector to obtain a so-called quantified biometric reference vector;
  forming a two-dimensional bar code from the quantified reference biometric vector and a flight identifier.

To capture the image, the application drives the image sensor 8 of the mobile phone 1 and prompts the future passenger to take a photograph of his/her face (commonly called "selfie"). For this purpose, the application can display text or graphic indications allowing the future passenger to take a photograph having a sufficient quality (in terms of exposure, sharpness, image contrast, facial dimensions on the image, etc.) to allow the extraction of the biometric characteristics.

The application then transfers the captured image via the data transport network 3 to the computer server 2, the program of which is designed to detect the position of the face in the image, align the face in the image, and then extract the biometric characteristics. Position detection and facial alignment produce an image having predetermined dimensions cropped on the face: these operations are known per se and will not be more detailed here.

Extraction is performed by at least one neural network driven by deep learning. The neural network is here a convolution network that is configured to provide a reference vector with a maximum size of 512 bytes. Only one neural network is used here, but it is possible to use several neural networks to do the extraction.

Preferably, the neural network here has an output layer comprising at most 128 neurons to provide an initial biometric reference vector (commonly referred to as a "biometric template") comprising 128 floating value coordinates.

The initial reference biometric vector which is then quantified to form the quantized reference biometric vector.

The quantification is less than or equal to four bits per value. It should be remembered that quantification consists in dividing all possible floating values into intervals, each of which is assigned a quantification value here on a maximum of four bits, and comparing each floating value of the initial biometric reference vector with the intervals: the floating value is then replaced by the quantification value associated with the interval which the floating value belongs to. Quantification is performed here on four bits so that the quantized biometric vector has a size of 512 bits (128 floating values times four bits of the quantization value replacing each floating value) or 64 bytes. Alternatively, the intervals can be different for each coordinate.

The neural network and the quantification operation are thus arranged so that the quantized biometric vector has a size of less than 200 bytes and allows recognition with a false rejection rate of at most about 3% and a false acceptance rate of at most about 0.0001%.

The two-dimensional bar code (commonly called "QR code" and symbolized in Q in the FIGURE) is formed in a traditional way except that the information to be included is the quantized biometric reference vector and a signature (the signature here has a size of 16 bytes).

The signature is an encrypted value corresponding here to the passenger's name and flight information (including the flight ID). Preferably, before the bar code is formed, the quantified reference biometric vector and the signature should be hashed. The bar code is then sent back to the application by the computer server 2. The bar code is here arranged so as to also contain: a surname and possibly a first name of the enlistment candidate; one or more piece(s) of information relating to a journey to be made by the enlistment candidate (flight number, boarding gate, destination, date and time of departure, train number, departure station, arrival station . . . ).

It should be noted that, after the capture, all or part of the operations allowing the constitution of the two-dimensional bar code can be carried out either within a mobile phone 1 or a computer server 2, and in particular:

the extraction of the biometric characteristics can be performed by the application within the mobile phone 1 or by the computer server 2 after transmission of the captured image;

the same goes for the formation of the bar code.

At the airport, the passenger is expected to launch the application in such a way that the virtual boarding pass can be displayed. The application is also designed to present, at the passenger's request, the bar code and other information about the flight, such as the time of departure. In addition, the application is preferably so designed as to connect to the airline's computer server 2 or to a dedicated computer server 4 at the airport which the computer server 2 is connected to and which the computer server 2 has communicated the passenger information to. This makes it possible to display information relating to check-in, boarding gate, possible delays . . . on a mobile phone 1, by means of a notification or an alert, The airport's computer server 4 is connected to a terminal 5 for access control to the boarding area. The terminal 5 includes a processor and a memory for performing a control process, as well as a two-dimensional bar code reader 6 and at least one camera 7 so arranged as to capture images of the faces of passengers standing in front of the terminal 5. The terminal 5 is so arranged as to control the opening of an access airlock under certain conditions.

To access the boarding area, the passenger commands the application to display the bar code on the screen 9 of his/her mobile phone 1, which he/she presents to the reader 6. The terminal 5 detects the bar code and controls the camera 7 to capture an image of the passenger's face.

The control program of the terminal 5 then carries out the steps of:
  extracting biometric characteristics from this image in the form of a candidate biometric vector;
  reading the bar code and extracting the quantified biometric reference vector and the signature therefrom;
  calculating a similarity score of the candidate biometric vector with the quantified reference biometric vector and deciphering the signature;
  validating or refusing recognition based on the similarity score, the accuracy of the passenger's name and the existence of a future flight corresponding to the flight identifier;
  opening the access airlock if recognition is validated and issuing an alert if recognition is refused.

The calculation of the similarity score is a distance between the two vectors. More specifically, the calculation of the similarity score includes a comparison of the distance to a threshold defined according to a desired rate of false acceptance and a desired rate of false rejection.

According to a first approach, the candidate biometric vector is binarized before the similarity score is calculated. The similarity score is here a Hamming distance the calculation of which is known per se.

The calculation of the Hamming distance is very fast. However, the binarization of the candidate biometric vector degrades the accuracy of the recognition.

A second approach is that the candidate biometric vector, which contains only real values, remains unchanged (without quantification), thus maintaining good recognition accuracy.

In a first version, the value of each component of the quantized reference biometric vector that is equal to 0 is replaced by −1 to obtain a transformed quantized reference biometric vector. The cosine distance between the transformed quantified reference biometric vector and the candidate biometric vector is then calculated.

The similarity score is then a cosine distance, the calculation of which is conventional.

In a second version, when designing the recognition algorithm, the mean value $\mu_i$ and the standard deviation $\sigma_i$ of each biometric vector component extracted from an image sample from a face database are calculated. Then, for each component of the quantified biometric reference vector:

if the value of the component i is 0, then the value of the component is replaced by $x_i = \mu_i - \sigma_i$;
if the value of the component i is 1, then the value of the component is replaced by $x_i = \mu_i \sigma_i$.

The similarity score is then a cosine distance calculated in a classical way.

Of course, the invention is not limited to the described embodiment but encompasses any alternative solution within the scope of the invention as defined in the claims.

In particular, the reference biometric vector can be stored in a graphic form (as in the two-dimensional bar code) but also in the electronic form, for example in a memory of an RFID integrated circuit contained in a document such as a passport, in a memory of an integrated circuit of an IC card, in a computer memory.

Although in the described implementation mode, it is the reference biometric vector that is provided by the neural network, it may be the candidate biometric vector. Both vectors can be obtained by means of a neural network and/or can be quantified.

The extraction can be performed in the mobile phone. This prevents biometric data from passing through a remote computer.

Depending on the type or number of neural networks used, the size of the biometric vector may differ from the one indicated. For example, with two or three neural networks, the biometric vector can have a size of 1024 or 1536 bytes. An example of a neural network and a usable learning method is the one described in the document "DeepVisage: Making face recognition simple yet with powerful generalization skills", Abul Hasnat et al, The IEEE International Conference on Computer Vision (ICCV), 2017, pp. 1682-1691.

The two-dimensional bar code can be stored in the memory of an electronic device such as a telephone or a multimedia tablet, or printed on a document such as a "paper" boarding pass.

It is possible to associate signature information to the reference biometric vector mixed by hashing with the flight identifier as well, which will include, for example, an integrity value calculated on the bits of the reference biometric vector obtained after hashing.

Other information may be mixed with the reference biometric vector, such as a date, the passenger's name or any other sequence of alphanumeric characters.

Instead of being carried out from a mobile phone, enlistment can be carried out from a check-in kiosk equipped with a biometric sensor and located, for example, at the airport.

Alternatively, the quantification used is a binarization. It should be recalled that a binarization is an operation consisting in comparing the value of each component of the quantified biometric reference vector to a threshold, and replacing the value of each component by 0 when the value of this component is less than or equal to the threshold and by 1 when the value of this component is above the threshold. For example, if the threshold is equal to 0, each component less than or equal to 0 is replaced by 0 and each component greater than 0 by 1. Thus, if the components of the initial reference biometric vector are each encoded on four bytes, i.e. 32 bits, and each of its components is binarized, the quantized reference biometric vector resulting from the binarization of the initial reference biometric vector is 32 times smaller than that of the initial reference biometric vector. Alternatively, the threshold may be different for each component. Preferably then, the threshold corresponds to an average value of each component. These mean values were calculated, at the time of designing the quantification algorithm, from a plurality of reference biometric vectors extracted from faces in a face database.

Other quantification modes are possible. For example, the range of possible values of each value of the initial biometric reference vector could be divided into four sub-intervals and this real value (initially encoded on 32 bits) could be replaced by a quantized value equal to 0, 1, 2 or 3 depending on the sub-interval which the real value belongs to. The quantized value is encoded on only two bits.

Upon completion of the quantification, the quantized reference biometric vector may have a different size from the one mentioned and for example a size of less than about 200 bytes, or even less than 100 bytes, or even less than 64 bytes and for example a size of 32 bytes.

The signature here results from an encoding of the name of the enlistment candidate and a piece of information relating to a journey he or she must make. Other data may be used to perform the signature.

Any data, in the form of a signature or not, can be encoded in the two-dimensional bar code The invention is applicable to biometric data other than face biometric data, and for example it may be applied to fingerprints, to irises, . . . .

The invention claimed is:

1. A biometric recognition method comprising:
during an enrollment stage, the steps of:
capturing an image of a portion of an individual's body; and
extracting from that image biometric characteristics in the form of a reference biometric vector; and
during a recognition stage, the steps of:
capturing an image of a portion of the body of a candidate for recognition;
extracting from that image biometric characteristics in the form of a candidate biometric vector;
calculating a similarity score between the candidate biometric vector and the reference biometric vector, only one of the two biometric vectors being quantified; and
validating or refusing recognition as a function of the similarity score.

2. The method according to claim 1, wherein the quantified biometric vector is the reference biometric vector.

3. The method according to claim 2, including, after extracting the reference biometric vector, a step of quantifying the reference biometric vector.

4. The method according to claim 1, wherein the similarity score is calculated as a distance between the two vectors and the method comprises the step of comparing the distance with a threshold that is defined as a function of a desired false acceptance rate and of a desired false rejection rate.

5. The method according to claim 4, wherein the distance is a cosine distance.

6. The method according to claim 1, wherein the quantification applied to the biometric vector is binarization.

7. The method according to claim 6, including, prior to calculating the score, a step of replacing the value of each component in the quantified biometric vector that is equal to 0 with the value −1 in order to obtain a transform quantified reference biometric vector.

8. The method according to claim 6, including, prior to calculating the score, a step of replacing the value of each component of the quantified reference biometric vector:
with $x_i = \mu_i - s_i$ if the value of the component i is 0; and
by $x_i = \mu_i \pm s_i$ if the value of the component i is 1;
where $\mu_i$ and $s_i$ are the mean value and the standard deviation of each component of biometric vectors extracted from a sample of face images.

9. The method according to claim 1, wherein the extraction is performed by a neural network trained by deep learning.

10. The method according to claim 9, wherein the neural network is a convolutional network.

11. The method according to claim 9, wherein the neural network has an output layer of 128 neurones.

12. The method according to claim 11, wherein quantification is performed so as to provide a biometric vector having a size less than 200 bytes and enabling a recognition with a false-rejection rate equal or inferior to 3% and a false acceptance rate equal or less than 0.0001%.

13. The method according to claim 12, wherein quantification is performed so as to provide a biometric vector having a size less than 100 bytes, preferably equal or inferior to 64 bytes, or even equal to 32 bytes.

14. The method according to claim 9, wherein the neural network is set to supply a reference vector having a size not greater than about 512 bytes.

* * * * *